United States Patent [19]
Batka et al.
[11] 3,969,134
[45] July 13, 1976

[54] PROCESS FOR USING CLEAR RINSING AGENTS IN MECHANICAL DISHWASHING

[75] Inventors: Heimold Batka, Dusseldorf-Reisholz; Theodor Altenschopfer, Dusseldorf-Holthausen, both of Germany

[73] Assignee: Henkel & Cie G.m.b.H., Dusseldorf-Holthausen, Germany

[22] Filed: Feb. 11, 1972

[21] Appl. No.: 225,603

[30] Foreign Application Priority Data
Feb. 12, 1971 Germany ............................ 2106819

[52] U.S. Cl. .............................. 134/26; 260/615 B; 252/89 R; 252/351; 252/DIG. 1
[51] Int. Cl.² .................... B08B 30/00; C07C 43/14
[58] Field of Search ................ 252/DIG. 1, 89, 135, 252/351; 260/615 B; 134/26

[56] References Cited

UNITED STATES PATENTS

| | | | |
|---|---|---|---|
| 3,350,462 | 10/1967 | Leary et al. | 260/615 B |
| 3,382,285 | 5/1968 | Egan et al. | 252/DIG. 1 |
| 3,504,041 | 3/1970 | Weipert et al. | 252/351 X |
| 3,549,539 | 12/1970 | Mallows | 252/89 X |
| 3,696,044 | 10/1972 | Rutledge | 252/180 |

FOREIGN PATENTS OR APPLICATIONS

| | | | |
|---|---|---|---|
| 950,844 | 2/1964 | United Kingdom | 260/615 B |

OTHER PUBLICATIONS

Union Carbide, "Tergitol S Biodegradable Surfactants," F-41410, pp. 2, 15, (1966).

Union Carbide, "Tergitol Nonionic Min-Foam Biodegradable Low-Foam Surfactant," F-41467, pp. 1, 2 (1966).

*Primary Examiner*—Morris O. Wolk
*Assistant Examiner*—Timothy W. Hagan
*Attorney, Agent, or Firm*—Hammond & Littell

[57] ABSTRACT

Process for rinsing of dishes in dishwashing machines having one or several clear-rinsing cycles using an aqueous solution of an adduct of from 5 to 20 moles of ethylene oxide and from 1 to 10 moles of propylene oxide to a secondary alkanol with a linear alkane chain of from 10 to 20 carbon atoms as clear-rinsing agents for use in the process.

5 Claims, No Drawings

PROCESS FOR USING CLEAR RINSING AGENTS IN MECHANICAL DISHWASHING

THE PRIOR ART

In mechanical dishwashing generally two cleaning cycles, usually separated by intermediate rinsing cycles with pure water are used. In the two cleaning cycles, different products are utilized. In the first or true cleaning cycle, alkaline-reacting agents are employed for the loosening and emulsifying of the food residues. In the after-rinsing or clear-rinsing bath, on the other hand, special clear-rinsing agents are employed. The latter should possess a good wetting power and be able to reduce the surface tension of the afterrinsing water to such a degree that it drains in a film-like manner from the dishes and leaves no visible deposits, such as lime spots or other impurities.

Because of the violent agitation of the liquor in the dishwasher, these clear-rinsing agents have to be as low-foaming as possible. The customary anionic wetting agents, however, such as higher-molecular-weight alkyl sulfates or alkyl sulfonates or aralkyl sulfonates are not generally usable because they foam too much. In practice, therefore, mostly nonionic tensides based on ethylene-oxide adducts to fatty alcohols, alkylphenols, or polypropylene glycols of higher molecular weights are employed. These products, however, were also found in actual practice to be not sufficiently low-foaming in the concentration range, required for a sufficient wetting effect.

These adducts have been found to cause disturbances due to excessive foam formation particularly in commercial dishwashing machines which have a very high rate of water circulation and a very high return rate of the clear-rinsing liquor into the main rinsing cycle. The same difficulties may also arise in home dishwashing machines. Even with the use of relatively low-foaming ethylene-oxide adducts, it is therefore necessary to add anti-foaming agents to the clear-rinsing agents. Suitable nonionic alkoxylation products are those which are slightly soluble at rinsing temperatures, such as ethylene-oxide adducts to higher alcohols or alkyl phenols with a low degree of ethoxylation or suitable adducts of ethylene oxide and propylene oxide. Such products possess, however, no wetting effect at the application temperatures and thus present a burden for the clear-rinsing agent.

In addition to this, the applied wetting agents should possess a good biological degradability and a low toxicity toward the organisms living in water. These features were not previously found to be available along with a good wetting and draining effect.

OBJECTS OF THE INVENTION

An object of the invention is the development of lowfoaming and biologically-degradable clear-rinsing agents for mechanical dishwashing with a good wetting and draining effect toward hard surfaces.

Another object of the invention is the development in the process for the mechanical washing of dishes which comprises subjecting dirty dishes to the action of a washing solution, subjecting the washed dishes to at least one clear-rinsing solution and recovering said washed dishes, the improvement consisting of utilizing an aqueous solution containing from 0.01 to 1.0 grams per liter of a clear-rinsing agent consisting essentially of (a) from 50% to 100% by weight of said clear-rinsing agent of an adduct of from 5 to 20 moles of ethylene oxide and from 1 to 10 moles of propylene oxide to a secondary alkanol having a linear alkane chain of from 10 to 20 carbon atoms and (b) from 0 to 50% by weight of said clear-rinsing agent of an adduct of from 5 to 10 moles of ethylene oxide to a secondary alkanol having a chain length of from 11 to 15 carbon atoms, as said at least one clear-rinsing solution.

It is another object of the present invention to provide a clear-rinsing agent for automatic dishwashing comprising a nonionic low-foaming tenside adduct having from 5 to 20 moles of ethylene oxide and 1 to 10 moles of propylene oxide to each mole of secondary aliphatic alcohol having a linear alkyl chain of from 10 to 20 carbon atoms.

It is a further object of the present invention to provide a process for utilizing a clear-rinsing agent that overcomes all the above problems.

These and other objects of the invention will become more apparent as the description thereof proceeds.

DESCRIPTION OF THE INVENTION

The present invention provides a development in the process for mechanical washing of dishes which comprises subjecting dirty dishes to the action of a washing solution, subjecting the washed dishes to at least one clear-rinsing solution and recovering said washed dishes, the improvement consisting of utilizing an aqueous solution containing from 0.01 to 1.0 grams per liter of a clear-rinsing agent consisting essentially of (a) from 50% to 100% by weight of said clear-rinsing agent of an adduct of from 5 to 20 moles of ethylene oxide and from 1 to 10 moles of propylene oxide to a secondary alkanol having a linear alkane chain of from 10 to 20 carbon atoms and (b) from 0 to 50% by weight of said clear-rinsing agents of an adduct of from 5 to 10 moles of ethylene oxide to a secondary alkanol having a chain length of from 11 to 15 carbon atoms, as said at least one clear-rinsing solution.

The problems of the prior art are solvent by the use of a clear-rinsing agent containing compounds which are exclusively wetting agents and which eliminates the use of anti-foaming agents or other foam depressors. This clear-rinsing agent for automatic dishwashing comprises a nonionic low-foaming tenside adduct having from 5 to 20 moles of ethylene oxide and 1 to 10 moles of propylene oxide to each mole of secondary alkanol having a linear alkyl chain of from 10 to 20 carbon atoms.

Preferably the clear-rinsing agent of the invention is added in the form of an aqueous concentrate for clear-rinsing solutions for automatic dishwashing consisting of (A) from 30% to 70% by weight of water and (B) from 30% to 70% of a clear-rinsing agent consisting essentially of (a) from 50% to 100% by weight of an adduct of from 5 to 20 moles of ethylene oxide and from 1 to 10 moles of propylene oxide to a secondary alkanol having a linear alkane chain of from 10 to 20 carbon atoms and (b) from 0 to 50% by weight of an adduct of from 5 to 10 moles of ethylene oxide to a secondary alkanol having a chain length of from 11 to 15 carbon atoms, wherein said clear-rinsing agent further contains (1) from 0 to 40% by weight, based on the weight of said clear-rinsing agent of a water-soluble lower organic carboxylic acid having from 2 to 6 carbon atoms and sequestering properties toward salts causing water hardness and (2) from 0 to 40% by weight, based on the weight of said clear rinsing agent of a water-miscible lower alcohol.

For the preparation of the adducts, the starting materials are linear secondary alkanols having a chain length of 10 to 20 carbon atoms. Preferred alcohols are those having a chain length of 11 to 15 carbon atoms or their mixtures. The alcohols are prepared in a known manner, for instance, by air-oxidation of straight-chain paraffins in the presence of boron trioxide. Generally the alcohols are present as mixtures of different chain lengths, whose secondary hydroxyl group is statistically distributed over the carbon chain.

The reaction of these alcohols with alkylene oxides is carried out in a known manner in the presence of acidic or alkaline catalysts, preferably with application of higher temperatures and pressures. First, 5 to 20 moles of ethylene oxide, optionally in several reaction steps with different catalysts, are reacted with 1 mole of alcohol or alcohol mixture. The alkylene oxide adducts are further reacted under suitable reaction conditions with 1 to 10 moles of propylene oxide. Preferably the adduct starting materials contain 5 to 10 moles of ethylene oxide to each mole of alcohol. To these materials 1 to 5 moles of propylene oxide are added. The ratio of ethylene oxide to propylene oxide is in the range of about 1 : 0.05 to 2, preferably 1 : 0.2 to 1.

The clear-rinsing agents of the invention possess the desired and advantageous properties of being extremely lowfoaming or practically non-foaming. They also possess a high degree of water solubility at rinsing temperatures (50° to 70°C), as well as showing a clear wetting effect toward the rinsed utensils. These properties are not expected from the teachings of the prior art, since known adducts of ethylene oxide and propylene oxide to primary alcohols are very intensively foaming or since known adducts comprising a higher concentration of propylene oxide do not possess satisfactory solubility and wetting properties.

The claimed ethylene oxide propylene oxide adducts may be combined with such adducts that exclusively contain ethylene oxide added to the named secondary alcohols. To achieve this particular embodiment, the adducts are comprised by from 5 to 10 moles of ethylene oxide to secondary alcohols having chain lengths of 11 to 15 carbon atoms. Such combinations possess, however, an increased tendency to foam formation; and for this reason not more than 50% by weight of the ethylene oxide propylene oxide adducts can be replaced by the named ethylene oxide adducts.

The adducts exhibit an excellent draining and clear-drying effect toward the conventional dish washing utensils, such as porcelain plates, metal cutlery and particularly glasses, that are considered to have a particularly difficult spotting problem in this respect. These adducts are, therefore, excellently suited for the clear-rinsing of dishes after a preceding cleaning cycle, for instance with alkaline detergents. Adduct concentrations of about 0.05 gm/l produce a drop-free, film-like draining of the clear-rinsing liquor from the dishes. The adducts are sufficiently biologically degradable, especially if the polyglycol chain length does not substantially surpass about 15 alkylene oxide units, which is preferred. The claimed products or combinations are applied in the clear-rinsing bath in concentrations of from about 0.01 to 1.0 gm/l, preferably 0.05 to 0.6 gm/l. The applied concentrations depend to a certain degree upon the kind of surface to be cleaned and are usually not influenced by the water hardness. Plastic surfaces in particular require a somewhat higher amount of clear-rinsing agents. The application of the adducts is preferably carried out in the form of aqueous or dilute alcoholic solutions with adduct contents of from 10 to 60% by weight of the total weight of the solution. As solvents in the alcoholic solution it is preferable to use water-miscible lower alcohols such as ethanol, propanol, isopropanol, ethylene glycol, propylene glycol, mono-ethyl ether of ethylene glycol and the mixtures thereof. If the adducts themselves are liquid they can also be used without solvents.

The adduct solutions or concentrates are appropriately added with the aid of automatic dispensing devices which are customary for such purposes; or they are manually added to the clear-rinsing liquor.

The invention also involves in the process for the mechanical washing of dishes which comprises subjecting dirty dishes to the action of a washing solution, subjecting the washed dishes to at least one clear-rinsing solution and recovering said washed dishes, the improvement consisting of utilizing an aqueous solution containing from 0.01 to 1.0 grams per liter of a clear-rinsing agent consisting essentially of (a) from 50% to 100% by weight of said clear-rinsing agent of an adduct of from 5 to 20 moles of ethylene oxide and from 1 to 10 moles of propylene oxide to a secondary alkanol having a linear alkane chain of from 10 to 20 carbon atoms and (b) from 0 to 50% by weight of said clear-rinsing agent of an adduct of from 5 to 10 moles of ethylene oxide to a secondary alkanol having a chain length of from 11 to 15 carbon atoms, as said at least one clear-rinsing solution.

If the rinsing is effected with hard water, lower organic carboxylic acids with 2 to 6 carbon atoms may be added to the concentrates or the clear-rinsing liquor for the avoidance of lime incrustations and lime hazes on the rinsed dishes. Acids are preferred that are physiologically inocuous and that possess sequestering properties toward the hardness causing salts, such as tartaric acid, lactic acid, glycolic acid and particularly citric acid. The optional addition of acid in the clear-rinsing concentrate amounts to about 10% to 40% by weight.

The following specific examples are illustrative of the invention without being limitative in any manner.

EXAMPLES

A. FOAMING BEHAVIOR

In a foaming test the foam behavior of different clear-rinsing agents or mixtures of them were examined. The test results, shown in Table I, demonstrate the extraordinarily favorable low foaming behavior of the claimed agents.

At a dosage level of 1 gm/l of clear-rinsing agents, the compounds or mixtures, listed in Table I, were stamped 20 times in measuring cylinder with a perforated disk and subsequently the foam height in centimeters after 10, 30 and 60 seconds was recorded. Foaming heights above 20 cm are marked by *x*. The city water used had a dH (degrees German hardness) of 16°. The residue of the concentrates, missing to 100%, is always water.

The abbreviations used in the Tables and Examples are:

EO = moles of ethylene oxide

PrO = moles of propylene oxide $C_{13}$-Sec. Alkanol = a secondary alkanol having carbon chains with 11 to 15 carbon atoms in statistical distribution, average 13 carbon atoms.

TABLE I

| Example No. | Concentration = 1 gm agent per liter solution | Foam height in cm. for City water at 50°C after 10 sec. | 30 sec. | 60 sec. | Foam height in cm. for permutite softened water at 50°C after 10 sec. | 30 sec. | 60 sec. |
|---|---|---|---|---|---|---|---|
| 1 | $C_{13}$-Sec. Alkanol + 7 EO/2PrO | 4.8 | 4.2 | 3.3 | 5.0 | 4.8 | 3.4 |
| 2 | $C_{13}$-Sec. Alkanol + 7 EO/3PrO | 1.0 | 0.9 | 0.8 | 1.0 | 0.9 | 0.8 |
| 3 | $C_{13}$-Sec. Alkanol + 7 EO/5PrO | 0.6 | 0.6 | 0.6 | 0.6 | 0.6 | 0.6 |
| 4 | $C_{13}$-Sec. Alkanol + 9 EO/3PrO | 4.8 | 3.7 | 3.2 | 5.9 | 4.0 | 3.6 |
| 5 | $C_{13}$-Sec. Alkanol + 9 EO/5PrO | 2.5 | 1.4 | 1.3 | 2.1 | 1.5 | 1.5 |
| 6 | 33% $C_{13}$-Sec. Alkanol + 7 EO<br>67% $C_{13}$-Sec. Alkanol + 7 EO/5PrO | 4.0 | 3.5 | 2.5 | 3.4 | 2.7 | 2.4 |
| 7 | 50% $C_{13}$-Sec. Alkanol + 7 EO/3PrO<br>50% Citric acid | 0.7 | 0.7 | 0.6 | 0.9 | 0.8 | 0.8 |

B. DRAINING BEHAVIOR

The draining behavior of the clear-rinsing agent was determined on Makrolon dishes at 50°C and in water having a German hardness of 16°; the results are listed in the following Table II. The concentrations listed are those at which a continuous water film was attained on the cleaned Makrolon dishes. The foam height figures were measured in an intensive foam instrument that simulates the conditions in a commercial dish-washing machine. It can be seen from Table II that the substances of the present invention are characterized by a superior draining behavior as well as by a superior low-foaming behavior. A comparison with a known adduct (8 moles of ethylene oxide to nonylphenol) shows particularly that there is a large reduction in the tendency for foaming.

TABLE II

| Ex. No. | | Draining effect on Makrolon dishes gm agent per liter solution | Foam height in the intensive foam instrument in mm |
|---|---|---|---|
| 2 | $C_{13}$-Sec. Alkanol + 7EO/3PrO | 0.20 | 10 |
| 3 | $C_{13}$-Sec. Alkanol + 7EO/5PrO | 0.25 | 8 |
| 4 | $C_{13}$-Sec. Alkanol + 9EO/3PrO | 0.20 | 75 (60°C) |
| 5 | $C_{13}$-Sec. Alkanol + 9EO/5PrO | 0.25 | 65 |
| For comparison: | | | |
| Nonylphenol + 8 EO | | 0.08 | 345 |

C. BIOLOGICAL DEGRADABILITY

The biological degradability of the adducts of the invention were measured in the known "closed bottle test" in order to determine the biochemical oxygen requirement in percent of the theory ("%B.O.D.T."). According to past experience, a "% B.O.D.T."-value of 40% or more corresponds to a good to very good degradability. The numerical results are summarized in the following Table III:

TABLE III

| Example No. | Substance | % B.O.D.T. after 30 days |
|---|---|---|
| — | $C_{13}$-Sec. Alkanol + 7 EO | 65 |
| — | $C_{13}$-Sec. Alkanol + 9 EO | 58 |
| — | $C_{13}$-Sec. Alkanol + 7 EO/1PrO | 60 |
| 1 | $C_{13}$-Sec. Alkanol + 7 EO/2PrO | 51 |
| 2 | $C_{13}$-Sec. Alkanol + 7 EO/3PrO | 48 |
| 3 | $C_{13}$-Sec. Alkanol + 7 EO/5PrO | 41 |

EXAMPLE 8

A clear-rinsing agent having a good effectiveness in commercial dish-washing machines was prepared according to the following composition in which the percent is percent by weight based on the total solution weight:

16% of $C_{13}$-Sec. Alkanol + 9 EO/5 PrO
35% of citric acid
7% of ethanol
42% of water The clear-rinsing effect was found to be good for a concentration range from 0.05 – 0.7 gm/l. The foam evolution is extraordinary low, if a liquor temperature of at least 50°C is maintained.

EXAMPLE 9

A clear-rinsing agent, particularly useful for home dish-washing machines has the following composition in which weight percent is the same as above:

20% of $C_{13}$-Sec. Alkanol + 9 EO/3 PrO
20% of citric acid
5% of mono-ethyl ether of ethylene glycol
55% of water The clear-rinsing effect is good over a concentration range from 0.1 – 1.0 gm/l. The foam evolution is sufficiently low, if a liquor temperature of at least 50°C is maintained.

EXAMPLE 10

A clear-rinsing agent, particularly useful for commercial dish-washing machines has the following composition in which weight percent is the same as above:

40% of $C_{13}$-Sec. Alkanol + 7 EO/5 PrO
60% of water

The clear-rinsing effect is very good over a concentration range from 0.1 – 0.7 gm/l. The foam evolution is extremely low.

EXAMPLE 11

A clear-rinsing agent useful for automatic dish-washing has the following composition in which weight percent is the same as above:

10% of $C_{13}$-Sec. Alkanol + 7 EO/2 PrO
25% of citric acid
55% of water
10% of ethanol The clear-rinsing effect is good over a concentration range from 0.2 – 1.0 gm/l. The foam evolution is very slight, if a liquor temperature of at least 50°C is maintained.

EXAMPLE 12

A clear-rinsing agent, particularly for home dishwashing machines, has the following composition in which weight percent is defined above:

10% of $C_{13}$-Sec. Alkanol + 7 EO/5PrO
10% of $C_{13}$-Sec. Alkanol + 7 EO
20% of citric acid
60% of water The clear-rinsing effect is good over a concentration range from 0.1 – 1.0 gm/l. The foam evolution is sufficiently low, if a liquor temperature of at least 50°C is maintained.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. In the process for the mechanical washing of dishes which comprises subjecting dirty dishes to the action of a washing solution, subjecting the washed dishes to at least one clear-rinsing solution and recovering said washed dishes, the improvement consisting of utilizing an aqueous solution containing from 0.01 to 1.0 grams per liter of a clear-rinsing agent consisting essentially of (a) from 50% to 100% by weight of an adduct of first from 5 to 20 moles of ethylene oxide and then from 1 to 10 moles of propylene oxide to a secondary alkanol having a linear alkane chain of from 10 to 20 carbon atoms and (b) from 0 to 50% by weight of an adduct of from 5 to 10 moles of ethylene oxide to a secondary alkanol having a chain length of from 11 to 15 carbon atoms, as said at least one clear-rinsing solution.

2. The process of claim 1 in which said adduct of (a) is the adduct of from 5 to 10 moles of ethylene oxide and from 1 to 5 moles of propylene oxide to a secondary alkanol having a linear alkane chain length of 11 to 15 carbon atoms, whereby the mole ratio of ethylene oxide to propylene oxide is 1:0.2 to 1.

3. The process of claim 1 wherein said clear-rinsing solution contains a further content of from 0 to 40% by weight, based on the total weight of said clear-rinsing agent of a water-soluble lower organic carboxylic acid having from 2 to 6 carbon atoms and sequestering properties towards salts causing water hardness.

4. An aqueous concentrate for clear-rinsing solutions for automatic dishwashing consisting of (A) from 30% to 70% by weight of water and (B) from 30% to 70% of a clear-rinsing agent consisting essentially of (a) from 50% to 100% by weight of an adduct of first from 5 to 20 moles of ethylene oxide and then from 1 to 10 moles of propylene oxide to a secondary alkanol having a linear alkane chain of from 10 to 20 carbon atoms and (b) from 0 to 50% by weight of an adduct of from 5 to 10 moles of ethylene oxide to a secondary alkanol having a chain length of from 11 to 15 carbon atoms, wherein said clear-rinsing agent further contains (1) from 0 to 40% by weight, based on the weight of said clear-rinsing agent of a water-soluble lower organic carboxylic acid having from 2 to 6 carbon atoms and sequestering properties toward salts causing water hardness and (2) from 0 to 40% by weight, based on the weight of said clear-rinsing agent of a water-miscible lower alcohol.

5. The aqueous concentrate of claim 4 in which said adduct of (a) is the adduct of from 5 to 10 moles of ethylene oxide and from 1 to 5 moles of propylene oxide to a secondary alkanol having a linear alkane chain length of 11 to 15 carbon atoms, whereby the mole ratio of ethylene oxide to propylene oxide is 1:0.2 to 1.

* * * * *